United States Patent [19]

Volante et al.

[11] Patent Number: 5,087,703
[45] Date of Patent: Feb. 11, 1992

[54] PROCESS FOR SYNTHESIS OF FK-506 INTERMEDIATES

[75] Inventors: Ralph P. Volante, East Windsor; David Askin, Edison; Ichiro Shinkai, Westfield; Kenneth M. Ryan, Clark, all of N.J.

[73] Assignee: Merck & Co., Inc., Rahway, N.J.

[21] Appl. No.: 508,153

[22] Filed: Apr. 11, 1990

Related U.S. Application Data

[63] Continuation of Ser. No. 149,464, Jan. 28, 1988, abandoned.

[51] Int. Cl.$^5$ .......................................... C07D 207/08
[52] U.S. Cl. .................................................. 548/406
[58] Field of Search ................ 548/406, 540; 549/214, 549/323

[56] References Cited

PUBLICATIONS

Evans, et al.; Tetrahedron Letters, 21 (1980), pp. 4233–4236.
Greene, "Protective Groups in Org. Syn", (1981), pp. 293–302; Wiley, N.Y.
Tanaka, et al.; J. Am. Chem. Soc., 109, (1987), pp. 5031–5032.
Askin, et al.; Tetrahedron Letters, 29 (1988), pp. 277–280.
Greger, J. Org. Chem., 37 (1972), pp. 1907–1918.
Iwai, et al.; Bull. Chem. Soc. Japan, 50 (1977), pp. 242–247.
Scheeren, et al.; Tetrahedron Letters, (1979), pp. 2925–2928, No. 31.
Donaubauer; Tetrahedron Letters, (1980), pp. 2771–2772, 21.
Yamaguchi, et al.; Tetrahedron Letters, 25 (1984), pp. 1159–1162.
Brown, et al.; J. Chem. Soc. Chem. Commun. (1985); pp. 1446–1447.
Davies, et al.; Tetrahedron Letters, 26 (1985), pp. 4815–4818.
Hatakeyama, et al.; J. Chem. Soc. Chem. Commun. (1985), pp. 1759–1761.
Hafele, et al.; Angew. Chem. Int. Ed. Engl. 25 (1986) pp. 87–89.
Babine, et al.; Tetrahedron Letters, 27 (1986), pp. 5791–5794.
Schreiber, et al.; J. Am. Chem. Soc.; 109 (1987), pp. 1525–1529.
Dale, et al.; J. Org. Chem., 34 (1969, pp. 2543–2549.
Sonnet, et al.; J. Org. Chem., 45 (1980), pp. 3137–3139.
Denis, et al.; Tetrahedron Letters, 22 (1981), pp. 1429–1430.
Davis, et al.; Tetrahedron Letters, 26 (1985), pp. 3539–3542.
Davis, et al.; J. Org. Chem., 52 (1987), pp. 5288–5290.
Gao, et al.; J. Am. Chem. Soc., 109 (1987), pp. 5765–5780.
Protective Groups in Organic Synthesis, by T. Green, pp. 293–302, [Date not available].
Tetrahedron Letters, vol. 29, No. 34, pp. 4245–4248, (1988), by D. Askin, et al.
Tetrahedron Letters, No. 52, pp. 5175–5178 (1978), by G. Stork, et al.
J. Organic Chemistry, vol. 46, No. 13, pp. 2831–2833, by T. Bruce Grindley, et al., (1981).

*Primary Examiner*—Joseph Paul Brust
*Attorney, Agent, or Firm*—Robert J. North; Charles M. Caruso; Hesna J. Pfeiffer

[57] ABSTRACT

A process is described for the synthesis of diastereomeric 2-methyl-4-hydroxy-5-protected-hydroxy-hept-6-en-prolinolamides, which are useful as intermediates in the synthesis of the $C_{10}$–$C_{18}$ chain of the macrolide structure for the immunosuppressant FK-506. These compounds are also useful as intermediates for preparing lactone ultraviolet radiation absorbers.

9 Claims, No Drawings

PROCESS FOR SYNTHESIS OF FK-506 INTERMEDIATES

CROSS REFERENCE TO RELATED APPLICATIONS

The present case is a Rule 62 continuation applications of U.S. Ser. No. 07/149,464, filed Jan. 28, 1988, now abandoned.

BACKGROUND OF THE INVENTION

1. Field of the Invention

This invention relates to a process for producing diastereoisomeric 2-methyl-4-hydroxy-5-protected-hydroxy-hept-6-en-prolinolamides useful as intermediates for producing ultraviolet radiation absorbers and as intermediates in synthesizing the $C_{10}$–$C_{18}$ fragment of FK-506 immunosuppressant.

2. Brief Disclosures in the Art

The novel 23-membered tricyclo-macrolide FK-506 very recently isolated and characterized by Tanaka, Kuroda, and co-workers, see JACS, 109. pp. 5031, 1987, and EPO Publication No. 0184162, has been shown to possess exceptional immunosuppressive activity. The potential usefulness of such an agent in bone marrow and organ transplantations coupled with its unique structural features has prompted many in the field to initiate an effort towards the total synthesis of FK-506. A highly diastereoselective synthesis of a protected C.10-C.18 subunit 1, in its correct absolute configuration, i.e.,

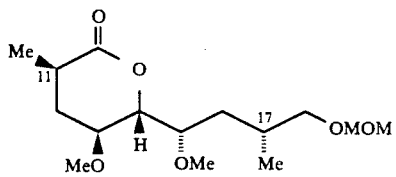

has already been achieved as reported by D. Askin, R. P. Volante, R. A. Reamer, K. M. Ryan and I. Shinkai in Tetrahedron Letters, 1988, in press.

However, what is needed is an overall general synthesis utilizing readily available starting materials which would allow the synthesis of all the possible diastereoisomers of the $C_{10}$–$C_{18}$ fragment of FK-506, some of which may exhibit greater immunosuppressant activity than the naturally occurring form itself.

SUMMARY OF THE INVENTION

It has been unexpectedly found that there is a reversal in enolate facial selectivity in the alkylation of epoxides by either (R) or (S) Z-dilithioprolinolpropionamide, e.g. following structures 6(R) or 6(S), to produce stereoisomeric 2-methyl-4-hydroxy-5-protected-hydroxy-hept-6-enprolinolamides, which allows the full range of $C_{10}$–$C_{18}$ subunit diastereoisomers to be synthesized by this process. For example, as shown below, the reaction of epoxide 4 with the dilithio salt 6(S), formed from 6(S) prolinol-propionamide by reaction with two equivalents of lithium diisopropylamide, yields the compound 7, being 2S-methyl-4S-hydroxy-5R-benzyloxy-hept-6-en-5-S-prolinolamide.

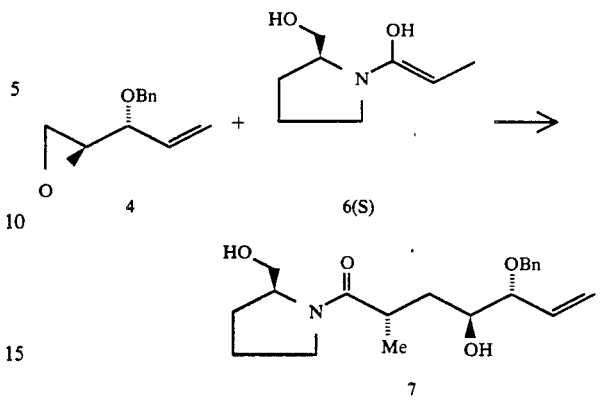

This is in contrast to the prior art (see reference of Evans, D. A., Takacs, J. M. Tetrahedron Lett. 1980, 21, 4233) which would have predicted the 2-methyl radical to have the same beta (wedge) configuration as the —CH$_2$OH prolinol group, i.e.

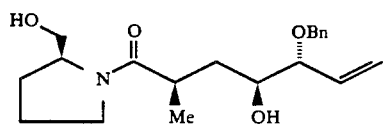

In accordance with the present invention there is provided an alkylation process comprising the step of reacting structures I and II to yield III, as shown by the following sequence:

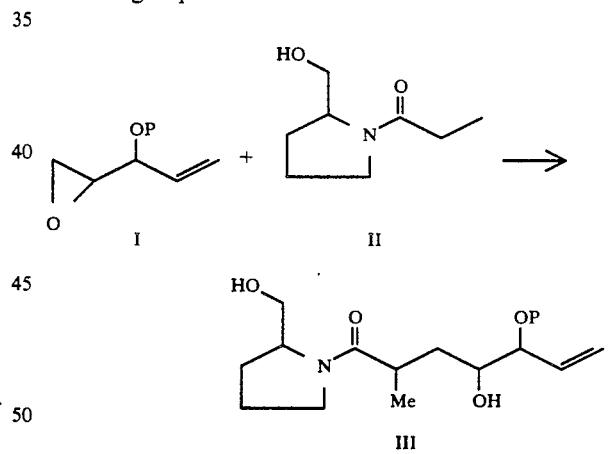

wherein P is a hydroxy protecting group, removable by catalytic hydrogenation or mild acid hydrolysis, said process being conducted in the presence of a lithium secondary alkylamine salt, in the temperature range of −30° to +40° C., in an anhydrous inert non-hydroxylic organic solvent, under an inert atmosphere for a sufficient time to form III.

Also provided is a compound of the formula:

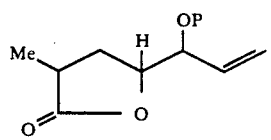

including all diastereoisomers thereof, where Me is methyl, and P is a hydroxy protecting group, removable by catalytic hydrogenation or mild hydrolysis, with the proviso that the bridgehead tertiary hydrogen and the OP group are in a syn configuration. These lactones are useful as ultraviolet radiation absorbers.

DETAILED DESCRIPTION OF THE INVENTION AND PREFERRED EMBODIMENTS

The process of the present invention can be readily understood by reference to the following Flow Chart A.

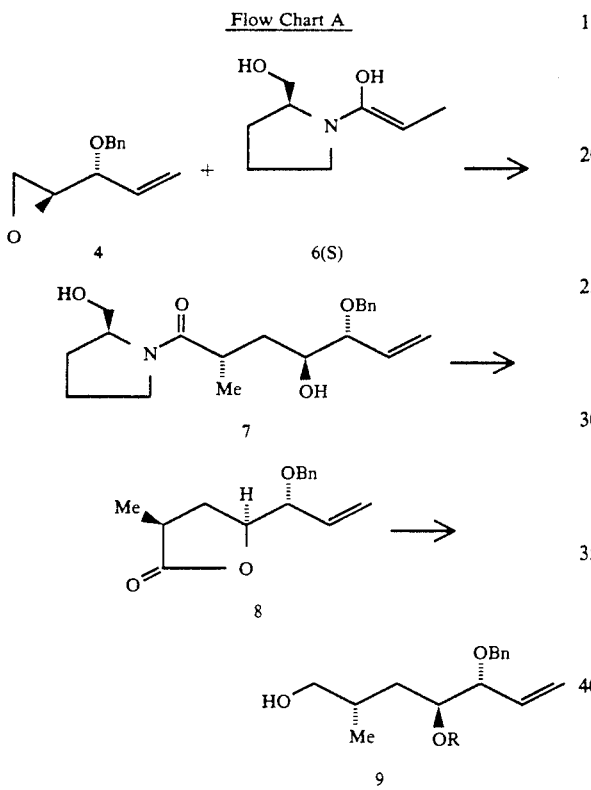

Because of the difficulty in illustrating an overall scheme including all possible diastereoisomers, the above scheme is shown only for one particular set of indicated isomers.

As is seen in this particular flow scheme, the starting material is (3R,4S)3-benzyloxy-4,5-epoxy-1-pentene 4, prepared by a modification of the procedure of R. E. Babine, Tetrahedron Letters, 27, pp. 5791, 1986, in which we used diisopropyl-D-tartrate as the chiral influencing agent, rather than the corresponding L-tartrate as used in Babine; and Gao, Y. et al., JACS, 109, pp. 5765, 1987, both hereby incorporated by reference for this purpose.

The corresponding 3S-4R isomer can also be prepared by the process of the above reference.

The symbols, P and P' as used herein, are conventional hydroxy protecting groups known in the act as exemplified in: U.S. Pat. No. 4,616,007; J. F. W. McOmie, "Protective Groups in Organic Chemistry", Plenum Press, London, New York, 1973; T. W. Greene, "Protective Groups in Organic Synthesis", Wiley, New York, 1981; "The Peptides", Vol. I, Schroeder and Luebke, Academic Press, London, New York, 1965, and in Houben-Weyl, "Methoden der Organischen Chemie", Vol. 15/1, Georg Thieme Verlag, Stuttgart, 1974, which are all hereby incorporated by reference for this particular purpose. The references also describe conventional methods for their attachment, use and removal. P and P' are chosen from the same overall class of hydroxy protecting groups but preferably are not the same group in the molecule. R as illustrated herein can also be a hydroxy protecting group as described herein for P or P' or a free hydroxyl.

Bn, benzyl, is a species representative of the hydroxyl protecting group P or P', which includes substituted benzyl, e.g. $X-Ph-CH_2-$, $X_2-Ph-CH_2-$, where $X=Cl$, Br, $NO_2$, $O-C_1-C_4$-alkyl, $O-C_6-C_{10}$-aryl, and the like, which are all known in the art and can be preferably removed, for example, by catalytic hydrogenation or acid hydrolysis. Preferred is unsubstituted benzyl. All values of P are operable in the illustrated scheme. Also included within P and P' is silyl hydroxy protecting group, being a triorganosilyl group, and by the term "organo" is meant $C_2-C_6$-alkyl, $C_6-C_8$-aryl and $C_3-C_{10}$-aralkyl, or mixtures thereof, where only trimethylsilyl is excluded. Representative examples include triethylsilyl, t-butyldimethylsilyl, benzyldimethylsilyl, phenyldiethylsilyl, diphenylmethylsilyl, triphenylsilyl, and the like. Preferred is t-butyldimethylsilyl.

The prolinolamide 6(S) is represented as the dilithio salt for convenience and is prepared in situ by reaction of the keto-alcohol form, i.e.,

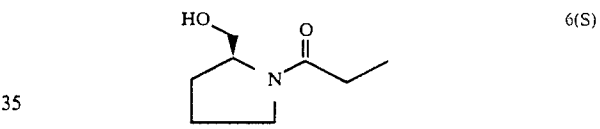

with two equivalents of an organo-lithium salt, e.g. n-butyl-lithium, or with 2 equivalents of a lithium dialkyl amide base e.g. lithium diisopropylamide.

Both the 6(S) and 6(R) prolinolamides can be prepared by the above-cited method of Evans, D. A. et al., hereby incorporated by reference for this purpose.

Generally, the formation of 7 is conducted by adding a solution of the lithium salt in an inert, anhydrous organic solvent, e.g. cyclic or acyclic hydrocarbon including hexane, cyclohexane, etc. to a solution of the secondary amine in anhydrous, inert solvent, e.g. tetrahydrofuran, at a temperature of about $-10°$ to $+5°$ C. under an inert atmosphere, e.g. dry nitrogen, and stirred for a sufficient time to form the dilithium salt.

The lithiating agent is an organolithium, preferably a lithium $C_1-C_6$-alkyl, or aryl lithium, e.g. n-butyllithium, s-butyllithium, methyllithium, isopropyllithium, phenyllithium, and the like, and preferably n-butyllithium.

The secondary amine contains two $C_1-C_{10}$-alkyl, cycloalkyl, aryl, aralkyl radicals, or mixtures thereof, including diethylamine, diisopropylamine, cyclohexylmethylamine, isopropyl-cyclohexylamine, hexamethyldisilazane, and the like, and preferably diisopropylamine.

The mixture is stirred at 0° C. for a short period and then a solution of the appropriate prolinolpropionamide in an anhydrous inert solvent, e.g. tetrahydrofuran, is added, in an amount such that the molar ratio of the lithium secondary amine salt: prolinolpropionamide is preferably 2:1. The solution is allowed to stir at room temperature for a short while, e.g. 1 hour, and then the epoxy pentene 4 in a solution of tetrahydrofuran is added keeping the temperature at about −20° to −30° C. for a sufficient time to form 7. Isolation and purification can be conducted, for example, by extraction into methylene chloride, followed by water washing and silica gel chromatography yields the desired 2S-methyl isomer in about a 10:1 molar ratio to the 2R-methyl isomer. Conventional apparatus for conducting the process can be used.

This electrophile dependent reversal of selectivity was not predicted by the prior art as in all known propionated derived prolinolamide alkylations the configuration at carbon 2 is controlled by alkylation of the Z-enolate from the least hindered face of the prolinolamide (anti to the CH$_2$O group). The epoxide examples illustrate a complete reversal of this prediction as in each example the epoxide must be alkylated from the more hindered (CH$_2$—OLi face) of the enolate.

The total diastereoisomers of III available by this synthetic process are (PO representing protected hydroxy and Me being methyl):

4+6(S)→2(S)—Me, 4(S)—OH, 5(R)—PO—(S)-prolinolamide
4+6(R)→2(R)—Me, 4(S)—OH, 5(R)—PO—(R)-prolinolamide
3(S), 4(R) epoxide+6(S)→2(S)—Me, 4(R)—OH-5(S)—PO—(S)-prolinolamide
3(S),4(R) epoxide+6(R)→2(R)-Me, 4(R)-OH-5(S)-PO-(R)

The novel lactone 8 can be prepared from 7 by treatment with refluxing 1:1 dioxane-aqueous 1N hydrochloric acid. The lactone 8 and all of the four (4) novel possible lactone diastereoisomers produced by this invention process are applicable as ultraviolet radiation absorbers. They can absorb the spectrum in the region of 220 to 270 millimicrons, and can be used, for example, in combination with relatively non-lightfast pigments to inhibit solar fading or color bleaching.

The lactone 8 can then be converted to the open chain diol 9 by the reduction with lithium aluminum hydride. The diol 9 can be used directly in a total synthesis, an epimer of the FK-506 molecule or its close analogues.

It has also been found that by converting the epoxide I to a triorganosilyl protected iodohydrin, IA, the other diastereoisomers can be prepared by reaction with II. This can be readily seen and understood by reference to the following Flow Chart B.

Flow Chart B

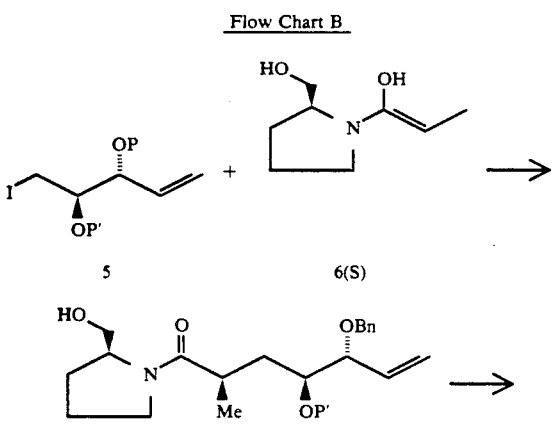

-continued
Flow Chart B

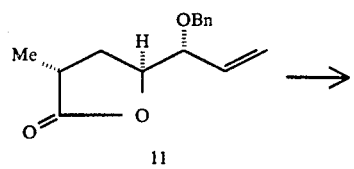

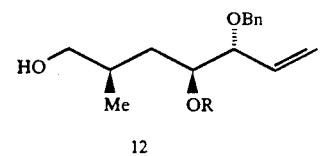

The triorganosilyl protected iodohydrin IA, as exemplified by 5 above, where (P) is benzyl and (P') is t-butyldimethylsilyl, is prepared from the corresponding epoxide 4 by reaction with a triorganosilyliodide, e.g. trimethylsilyliodide, in solution in an inert anhydrous solvent at −80° to −60° C. The reaction is stirred, the volatiles are removed, and the reaction mixture is then quenched with methanol. The methanol is removed and the free hydroxyl group is protected as a more stable silyl ether, e.g. t-butyl-dimethylsilyl, by treatment with the appropriate silyl triflate reagent (t-butyldimethylsilyltriflate), in a solvent, for example, toluene, methylene chloride, and the like in the presence of a base such as lutidine.

As is seen in the Flow Chart B, use of the iodohydrin leads to the 2R-methyl isomer as contrasted to the 2S-methyl isomer in Flow Chart A by use of the epoxide.

Isolation/purification methods for the product are conventional and the same as described above.

Conversion of the prolinol amide 10 to the lactone 11, and then to the open chain diol 12, can be conducted by the analogous procedures as described above.

The diastereoisomers of III obtainable by this process are:

5+6(S)→2(R)Me, 4(S)OH, 5(R)—PO—(S)-prolinolamide
5+6(R)→2(S)Me, 4(S)OH, 5(R)—PO—(R)-prolinolamide
5 mirror image+6(S)→2(R)—Me, 4(R)—OH, 5(S)PO—(S)-prolinolamide
5 mirror image+6(R)→2(S)—Me, 4(R)—OH, 5(S)PO-(R)-prolinolamide Thus, between use of the epoxide I, and the protected iodohydrin IA, 8 of the possible 16 diastereoisomers of III can be prepared.

The following examples are illustrative of the invention and should not be considered as being limitations on the scope of the instant invention.

EXAMPLE 1

(3R,4S)3-Benzyloxy-4,5-epoxy-1-pentene (4)

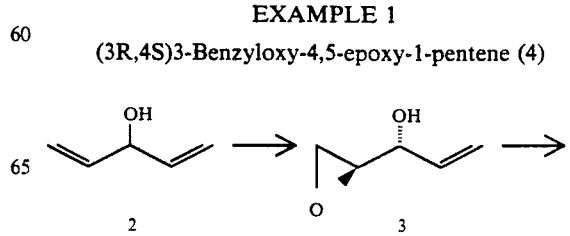

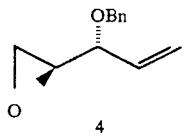

Prepared from 3-hydroxy 1,4-pentadiene by a modified procedure of R. E. Babine, Tetrahedron Letters, 1987, 27, 5791, using diisopropyl-D-tartrate instead of the L form.

Analysis showed: Optical Rotation: $[\alpha]_D^{25} = -25.3°$ $CH_2Cl_2$, C=1.03: IR ($CHCl_3$) $\lambda$max 1075 cm$^{-1}$; 13C NMR ($CDCl_3$, 75.5 MHZ) δ138.0, 134.4, 128.3, 127.58, 27.53, 119.4, 79.2, 70.5, 53.1, 44.7.

|   | Calc'd | Found |
|---|--------|-------|
| C | 75.76  | 75.86 |
| H | 7.42   | 7.55  |

EXAMPLE 2

2S-Methyl-4S-hydroxy-5R-benzyloxy-hept-6-en-(S)-prolinol amide (7)

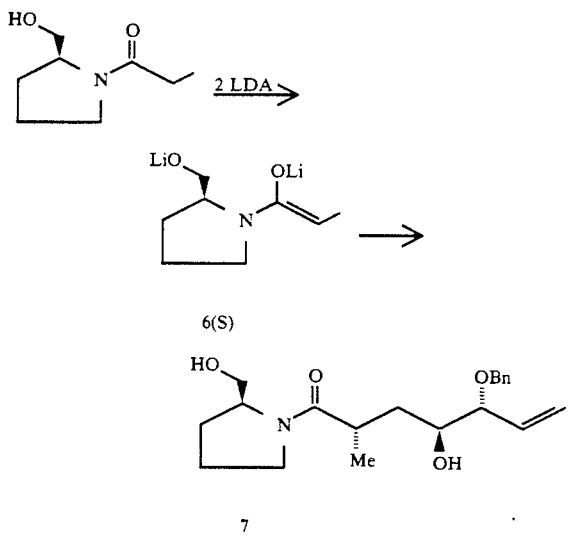

n-Butyllithium (2.15 ml of 1.6M solution in hexane, 3.44 mmol) was added to a solution of diisopropylamine (348 mg, 3.44 mmol) in tetrahydrofuran at 0°-2° C. The solution was stirred for 10 min. at 0° C. and then a solution of S-prolinol propionamide (280 mg, 1.78 mmol in 4 ml of tetrahydrofuran) was added. The solution was warmed to 25° C. over 30 min. and then was stirred at 22°-25° C. for 1 hr. The solution was cooled to −30° C. and (3R,4S)3-benzyloxy-4,5-epoxy-1-pentene 4 (64.4 mg, 0.339 mmol) in 4 ml of tetrahydrofuran was added while maintaining the reaction temperature at −20° to −28° C. The mixture was stirred at −30° C. for 18 hr. The mixture was then partitioned between 100 ml of methylene chloride and 25 ml of water. The aqueous phase was extracted with an additional 2×50 ml of methylene chloride. The combined organic phases were dried over sodium sulfate and concentrated to a yellow oil (354 mg). NMR analysis showed the presence of two diastereomeric products in a ratio of ca. 10:1. The diastereomers were separated by chromatography on silica gel eluting with 5% methanol in ethyl acetate. The 2S-methyl-4S-hydroxy diastereomer was obtained as the major product (300 mg) and the 2R-methyl diastereomer as the minor product (ca. 25 mg).

EXAMPLE 3

2-Oxo-3S-methyl-5S(1R-benzyloxyprop-2-en-1-yl)tetrahydrofuran (8)

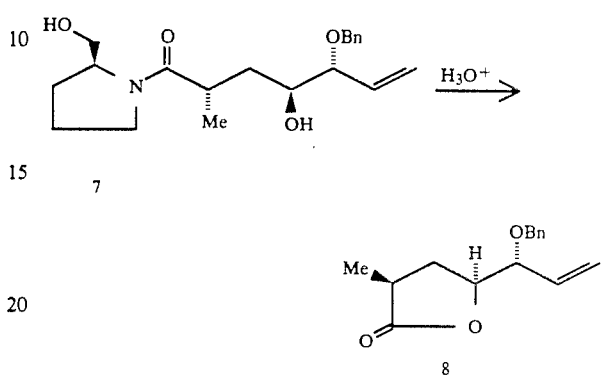

Prolinol amide 7 (307 mg, 0.88 mol) was dissolved in 42 ml of dioxane aqueous/1N hydrochloric acid (1:1) and the solution was heated at reflux temperature for 3 hr. The mixture was cooled to ambient temperature and ca. 125 ml of diethyl ether was added. The organic layer was separated and was washed successively with 20 ml of water, 20 ml of saturated sodium bicarbonated solution, and 20 ml of saturated sodium chloride solution. The organic layer was then dried over magnesium sulfate and concentrated in vacuo to give a crude oil which after column chromatography over silica gel eluting with hexanes/ethyl acetate (4:1) gave 165 mg (76%) of the lactone 8 as a yellow oil.

Analysis showed: Optical Rotation: $[\alpha]_D^{25}=30.6°$ $CH_2Cl_2$, C=1.04;

|   | Calc'd | Found |
|---|--------|-------|
| C | 73.15  | 73.15 |
| H | 7.37   | 7.51  |

IR($CHCl_3$) $\lambda$max 1770 cm$^{-1}$; $^{13}$C NMR ($CDCl_3$, 75.5 MHZ) δ 179.2, 137.8, 133.4, 128.3, 127.7, 127.6, 120.2, 79.9, 79.1, 70.8, 34.8, 31.0, 15.2.

EXAMPLE 4

(R,R)-2-t-Butyldimethylsiloxy-3-benzyloxy-5-penten-1-yl iodide (5)

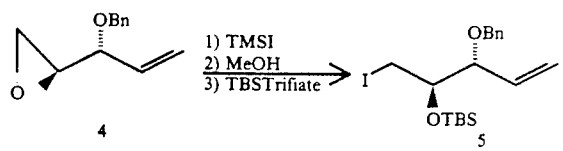

(3R,4S)3-Benzyloxy-4,5-epoxy-1-pentene 4 (530 mg, 2.78 mmol) was dissolved in anhydrous toluene (35 ml) and the solution was cooled to −78° C. Trimethylsilyliodide (586 mg, 2.93 mmol) was added via syringe and the mixture was stirred for 30 min. at −78° C. and then was warmed to 22°-25° C. over 45 min. The reaction was quenched by the addition of 20 ml of methanol. The methanol was removed in vacuo and the residual oil (875 mg) was dissolved in 15 ml of methylene chloride. 2,6-Lutidine (980 μl) and t-butyldimethylsilyl triflate (1.92 ml) were added sequentially and the mixture was aged at 22°–24° C. The solution was then cooled to 0° C. and methanol (340 μl, 8.4 mmol) was added. The mixture was aged at 0°–5° C. for 30 min. and was partitioned between 100 ml of diethylether and 50 ml of aqueous sodium bicarbonate solution. The ethereal layer was washed with 25 ml of saturated sodium chloride solution, dried over sodium sulfate, and concentrated to an oil (1.31 g). The crude oil was purified by column chromatography over silica gel eluting with hexanes/diethyl ether (25:1) to give 1.15 g of silyl iodide 5. The material was homogeneous by proton and carbon NMR.

Analysis showed: $^{13}$CNMR (CDCl$_3$, 75.5 MHZ) δ 138.2, 135.3, 128.3, 128.0, 127.6, 119.8, 83.0, 72.7, 70 9, 25.8, 18.1, 12.2, −4.3, −4.5.

|   | Calc'd | Found |
|---|--------|-------|
| C | 50.00  | 50.13 |
| H | 6.76   | 6.88  |
| I | 29.35  | 29.20 |

EXAMPLE 5

R-Methyl-4S-t-butyldimethylsiloxy-5R-benzyloxy-hept-6-en-(S)-orolinol amide (10)

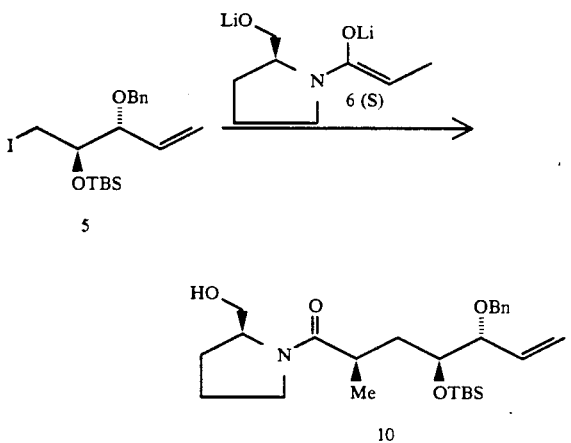

n-Butyllithium in hexane (17.7 ml of a 1.5M solution, 26.6 mmol) was added to solution of diisopropylamine (4.1 ml, 29.2 mmol) in tetrahydrofuran at 0° C. The resulting solution was stirred at 0° C. for 15 min. and a solution of S-prolinol propionamide (2.11 g, 13.4 mmol) in 5 ml of tetrahydrofuran was added over a 10 min. period while maintaining the temperature at 0°–5° C. The solution was warmed to 25° C. and was stirred for 1 hr. Iodide 5 (1.15 g, 2.66 mmol) in 10 ml of tetrahydrofuran was added dropwise and the resulting solution was aged at 22°–25° C. in the absence of light for 20 hr. The mixture was poured into 50 ml of water and was extracted with 100 ml of methylene chloride. The aqueous layer was back extracted with 50 ml of methylene chloride and the organic layers were combined. The combined organic layers were washed with 50 ml of saturated sodium chloride solution, dried over sodium sulfate, and concentrated in vacuo to an oil (2.97 g). Proton NMR showed a 10:1 selectivity for the 2R:2S methyl diastereomers.

EXAMPLE 6

2-Oxo-3R-methyl-5S-(1R-benzyloxyprop-2-en-1-yl)-tetrahydrofuran (11)

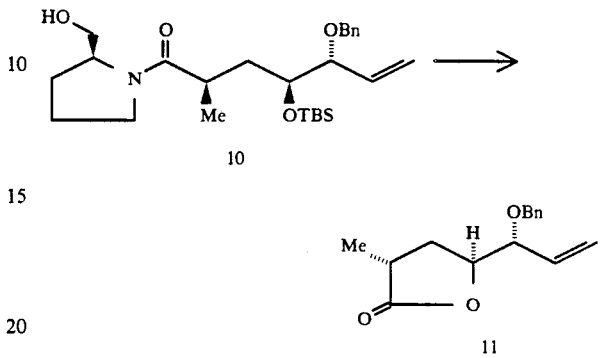

The crude prolinol amide 10 (2.97 g, 0.88 mmol) was dissolved in 100 ml of dioxane-aqueous hydrochloric acid (1:1) and the solution was heated at reflux temperature for 4 hr. The mixture was cooled to ambient temperature and 400 ml of diethyl ether was added. The organic layer was separated and was washed successively with 100 ml of water, 100 ml of saturated sodium bicarbonate solution, and 100 ml of saturated sodium chloride solution. The organic layer was dried over sodium sulfate and was concentrated in vacuo to give 753 mg of crude lactone 11 as a yellow oil. The desired 3R methyl-2-oxo-tetrahydrofuran 11 could be separated from the minor diastereomer 3S-methyl compound 8 by chromatography over silica gel eluting with hexanes/ethyl acetate (4:1), affording 447 mg of 11 (68% yield from 5).

Analysis showed: $[\alpha]_D^{25} = -14.1°$ CH$_2$Cl$_2$, C=0.411;

|   | Calc'd | Found |
|---|--------|-------|
| C | 73.15  | 72.98 |
| H | 7.37   | 7.19  |

IR(CHCl$_3$) λmax 1765 cm$^{-1}$; $^{13}$C NMR (CDCl$_3$, 75.5 MHZ) δ 180.6, 137.8, 133.5, 128.5, 127.8, 120.0, 81.1, 79.0, 71.3, 34.1, 30.2, 16.4; Ultraviolet absorption: 226 nm (ε142), 258 nm (ε 210).

EXAMPLE 7

The procedures of Examples 2 and 5 were also conducted utilizing 6(R) prolinolpropionamide, being the mirror image of 6(S), to yield: respectively, 2 (R) Me, 4(S) OH, 5(R) PO-(R)-prolinolamide and 2(S) Me, 4(S) OH, 5(R) PO-(R)-prolinolamide.

What is claimed is:

1. An alkylation process comprising the step of reacting Structures I and II to yield III, as shown by the following sequence:

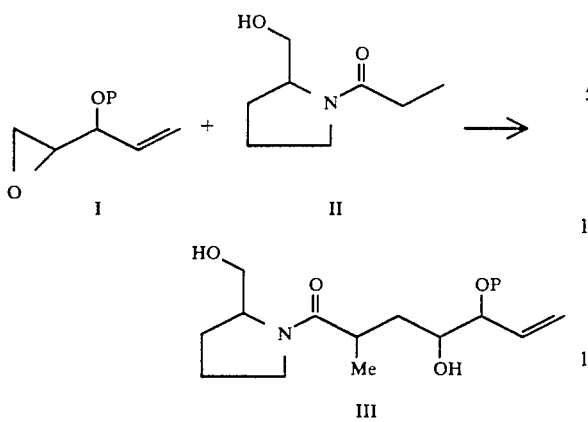

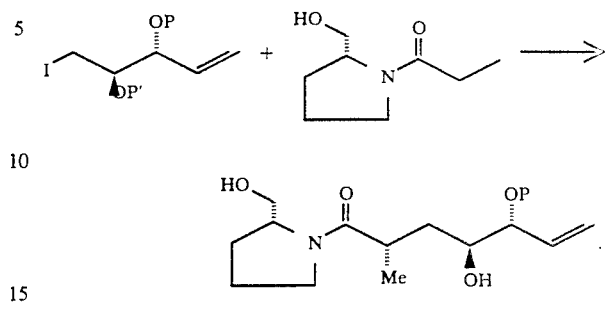

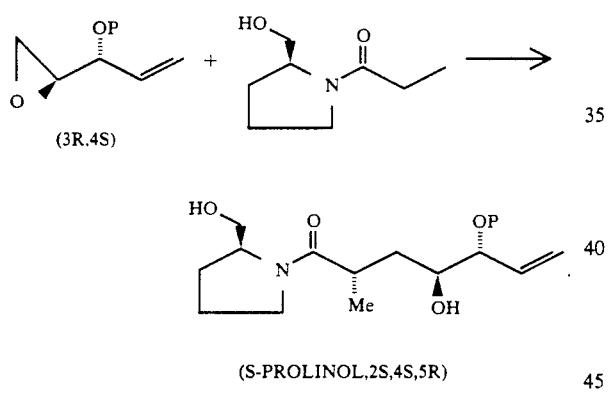

wherein P is a triorganosilyl protecting group, wherein "organo" is $C_2$–$C_6$ alkyl, $C_6$–$C_8$ aryl, $C_3$–$C_{10}$ aralkyl, or mixtures thereof, removable by catalytic hydrogenation or mild acid hydrolysis, said process being conducted in the presence of two equivalents of a lithium secondary di $C_1$–$C_{10}$ alkylamine salt, in the temperature range of $-10°$ to $+40°$ C., in an anhydrous inert non-hydroxylic organic solvent, under an inert atmosphere for sufficient time to form III.

2. The process of claim 1 wherein the structures in the process sequence are:

3. The process of claim 1 wherein said temperature range is from 0° to 25° C.

4. The process of claim 1 wherein said solvent is selected from halogenated alkanes, alkyl ethers or cyclic ethers.

5. The process of claim 1 wherein said lithium secondary amine salt is lithium diisopropylamide.

6. The process of claim 2 wherein the structures in the process sequence are:

7. The process of claim 2 wherein the structures in the process sequence are:

8. The process of claim 2 wherein the structures in the process sequence are:

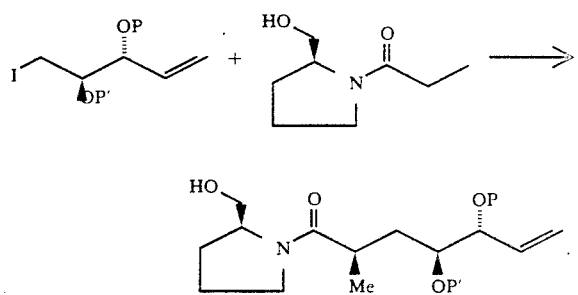

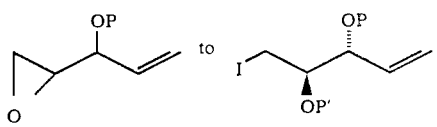

9. An alkylation process comprising the steps of converting

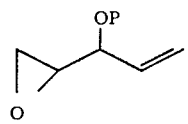

wherein P and P' are triorgano silyl protecting groups for hydroxyl, wherein "organo" is $C_2$–$C_6$ alkyl, $C_6$–$C_8$ aryl, $C_3$–$C_{10}$ aralkyl, or mixtures thereof; formed by reacting

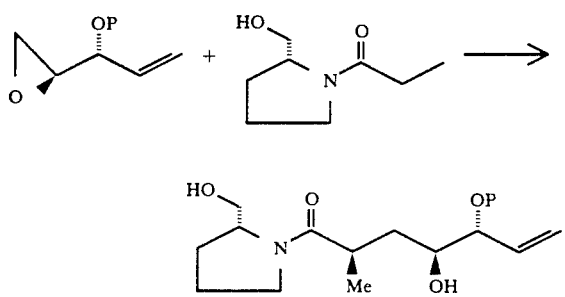

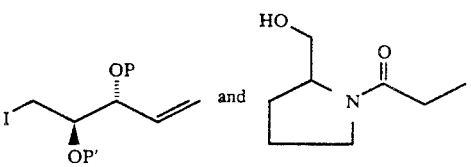

with a triorganosilyliodide in an inert non-hydroxylic anhydrous solvent in the temperature range of $-80°$ to $-60°$ C., under an inert atmosphere, and then conducting the reaction between at a temperature range of $-10°$ to $+40°$ C., in an anhydrous inert non-hydroxylic organic solvent, under an inert atmosphere for a sufficient time to form the product.

* * * * *